United States Patent [19]
Christoff et al.

[11] Patent Number: 6,071,119
[45] Date of Patent: Jun. 6, 2000

[54] DUAL MODE SELF-LIGATING ORTHODONTIC BRACKET

[75] Inventors: James D. Christoff, Birchwood, Minn.; John S. Kelly, Arcadia; Evangelos G. Georgakis, Alta Loma, both of Calif.

[73] Assignee: 3M Innovative Properties Company, St. Paul, Minn.

[21] Appl. No.: 09/218,929

[22] Filed: Dec. 22, 1998

[51] Int. Cl.[7] .................................................. A61C 3/00
[52] U.S. Cl. ............................................. 433/14; 433/13
[58] Field of Search ........................... 433/8, 9, 10, 11, 433/12, 13, 14

[56] References Cited

U.S. PATENT DOCUMENTS

| | | | |
|---|---|---|---|
| 5,474,445 | 12/1995 | Voudouris | 433/10 |
| 5,613,850 | 3/1997 | Wildman et al. | 433/10 |
| 5,630,715 | 5/1997 | Voudouris | 433/8 |
| 5,711,666 | 1/1998 | Hanson | 433/11 |
| 5,857,850 | 1/1999 | Voudouris | 433/11 |
| 5,863,199 | 1/1999 | Wildman | 433/10 |
| 5,890,893 | 4/1999 | Heiser | 433/11 |
| 5,908,293 | 6/1999 | Voudouris | 433/10 |
| 5,913,680 | 6/1999 | Voudouris | 433/10 |

FOREIGN PATENT DOCUMENTS

WO 98/20805   5/1998   WIPO .

*Primary Examiner*—Nicholas D. Lucchesi
*Attorney, Agent, or Firm*—James D. Christoff

[57] ABSTRACT

A self-ligating orthodontic bracket has a latch that is movable from a slot-open position to a first closed position or a second closed position. In the first closed position of the latch, the latch engages an archwire with sufficient force to provide active orthodontic therapy. In the second closed position, the effective labial-lingual dimension of the archwire slot is somewhat greater than the overall labial-lingual dimension of the archwire such that the bracket provides passive orthodontic therapy.

27 Claims, 8 Drawing Sheets

DUAL MODE SELF-LIGATING ORTHODONTIC BRACKET

BACKGROUND OF THE INVENTION

1. Field of the Invention

This invention broadly relates to brackets used in orthodontic treatment. More specifically, the invention relates to an orthodontic bracket having a latch for releasably retaining an archwire in an archwire slot of the bracket.

2. Description of the Related Art

Orthodontic therapy is a specialized type of treatment within the field of dentistry, and involves movement of malpositioned teeth to orthodontically correct locations. Orthodontic treatment often improves the patient's occlusion and typically enhances the aesthetic appearance of the teeth.

Many types of orthodontic treatment programs involve the use of a set of tiny appliances and wires that are commonly known collectively as "braces". During such treatment programs, small appliances known as brackets are fixed to the patient's anterior, cuspid and bicuspid teeth, and an archwire is inserted into a slot of each bracket. The archwire forms a track to guide movement of the teeth to orthodontically correct locations. End sections of the archwires are typically captured in tiny appliances known as buccal tubes that are fixed to the patient's molar teeth.

Many types of orthodontic brackets have archwire slots that are open on one side for insertion of the archwire, and bounded on remaining sides by a central body of the bracket tiewings or other structure. Brackets that are intended to be bonded to the patient's front tooth surfaces often have archwire slots that are open either on a buccolabial side (i.e., a side facing the patient's cheeks or lips) or an occlusal side (i.e., a side facing the outer tips of the teeth) of the archwire slot. Some brackets, however, are intended to be fixed to the lingual side of the patient's teeth (i.e., the side of the teeth facing the patient's tongue) and in that instance typically have an archwire slot that is open on a lingual side or on an occlusal side.

Many orthodontists use ligatures to connect the archwire to the brackets and to urge the archwire into an orientation of seating engagement in the archwire slot. One type of commercially available orthodontic ligature is a small, elastomeric O-ring. Orthodontic O-rings are installed by stretching the O-ring around small wings (known as "tiewings") that are connected to the bracket body on the gingival side (i.e., the side facing the patient's gingiva or gums) and on the occlusal side of the archwire slot. Once installed, the O-ring ligature extends around the tie wings as well as over the labial side of the archwire in order to urge the archwire toward a lingual wall of the archwire slot.

Metal ligatures, such as ligatures made of stainless steel, are also used to retain archwires in archwire slots of brackets. Metal ligatures are typically made of a short section of initially straight wire. During installation, the wire ligature is hooked around the tiewings and extended over the labial side of the archwire, and end sections of the ligature are then twisted together to form a loop to retain the ligature in place.

Unfortunately, some orthodontists are not entirely satisfied with elastomeric and metal ligatures. Such ligatures are somewhat time-consuming to install, during initial installation and also during reinstallation whenever replacement of the archwire or ligatures is desired. As can be appreciated, a savings in the amount of time needed for ligation can help to reduce the total time that the practitioner must spend with the patient and consequently aid in reducing the overall costs of orthodontic treatment.

Other disadvantages are also associated with elastomeric and metal ligatures. For example, there have been reports that polyurethane elastomeric ligatures have exhibited deformation and force decay during the course of treatment. In some instances, elastomeric ligatures are stained by food and beverages consumed by the patient and become somewhat unsightly. Metal ligatures often have sharp ends that may retain plaque and food debris and also may increase the risk of cross-infection.

In an effort to overcome the problems associated with conventional ligatures, a variety of orthodontic brackets have been proposed having various types of latches for coupling the archwire to the bracket. Such brackets are also known as self-ligating brackets. The latch comprises a clip, spring member, cover, shutter, bail or other structure that is connected to the bracket body for retaining an archwire in the archwire slot.

Examples of self-ligating orthodontic brackets having generally U-shaped ligating latch clips are described in U.S. Pat. Nos. 3,772,787, 4,248,588 and 4,492,573. In general, the clip of such brackets is slidably mounted on the bracket body, and a dental explorer or other small-tipped dental tool is used to move the clip relative to the body when needed in order to open or close the archwire slot. A self-ligating bracket known as the "Speed" brand bracket also has a movable, generally U-shaped clip for ligating the archwire to the bracket.

Other types of self-ligating brackets have latches that resemble swinging shutters or closures that pivotally move between a slot-open and a slot-closed position. For example, U.S. Pat. No. 4,712,999 has a rotatable cover plate that is pivotally connected at one end to a tiewing of the bracket along one side of the slot, and is releasably engagable at the other end with a tiewing that is located along the opposite side of the archwire slot. Other orthodontic brackets with swinging latches are described in U.S. Pat. Nos. 4,103,423, 5,516,284 and 5,685,711.

U.S. Pat. Nos. 4,371,337 and 4,559,012 describe self-ligating orthodontic brackets having latches that rotate about the longitudinal axis of the archwire slot. The latches of these references have a somewhat cylindrical shape that is rotatably received in a mating, cylindrical channel, and an outwardly extending arm is provided to assist in rotatably moving the latch between a slot-open and a slot-closed position.

A self-ligating orthodontic bracket that is described in U.S. Pat. No. 5,711,666 has a ligating latch that comprises a flexible flat spring member. One end of the spring member is fixed to the bracket body on one side of the archwire slot, and the opposite end of the spring member has notches that releasably engage latch sears or catches when the spring member is moved to a slot-closed position. To open the slot, the notches are disengaged from the catches and the spring member is bent to an orientation sufficient to enable the archwire to be removed from the archwire slot.

Other types of self-ligating orthodontic brackets have latches that comprise essentially flat plates that are slidable between a slot-open and a slot-closed position. Examples of such construction are shown in U.S. Pat. Nos. 5,094,614, 5,322,435 and 5,613,850. In general, the sliding latches described in those references move in upright channels that are located buccolabially of the archwire slot.

Another type of self-ligating bracket that has been proposed in the past has a latch that is made of a section of wire material that functions as a bail. The orthodontic brackets described in U.S. Pat. Nos. 4,149,314, 4,725,229 and 5,269,681 have wire-like latches that swing between a slot-closed position and a slot-open position. The orthodontic bracket described in U.S. Pat. No. 4,260,375 has a wire latch that is slidable between a slot-open and a slot-closed position.

Many of the self-ligating brackets described above as well as commercially-available self-ligating brackets have structure that is intended to prevent unintentional movement of the latch. It is undesirable, for example, for the latch to accidentally move to a slot-open position during the course of treatment since the archwire may disengage the bracket once the slot has been opened. Once the archwire has separated from the bracket, control over movement of the associated tooth is temporarily lost. In such instances, the patient must return to the orthodontist's office so that the wire can be re-inserted in the archwire slot in order to resume treatment.

It is also often desired to restrain movement of the latch in an opposite direction in some manner so that the latch does not unintentionally detach from the body of the bracket when the latch is opened. For example, the orthodontist may move the latch of each bracket to a slot-open position during the course of treatment in order to replace the archwire with an archwire having different characteristics. If the latch becomes separated from the bracket body during such procedures, the practitioner must interrupt the procedure to retrieve the latch and replace it on the bracket body.

Self-ligating orthodontic bracket and archwire systems can be classified as either active or passive. In the passive system, the overall width of the archwire in a labial-lingual direction is less than the effective labial-lingual depth of the archwire slot when the latch is closed, resulting in a certain amount of space between the archwire and either the labial or lingual extent of the archwire slot. Some practitioners believe that the passive system presents less friction between the archwire and the bracket than would otherwise be possible, and that such reduced friction facilitates sliding movement of the bracket along the archwire to such an extent that overall treatment time is reduced.

By contrast, in active systems there is no space in a labial-lingual direction in the archwire slot between the archwire and the effective labial-lingual extent of the archwire slot. As a result, one side of the archwire of such systems is typically seated in the slot while the opposite side of the archwire is in contact with the latch. Oftentimes, the latch of such systems is resilient and functions as a spring member to urge the archwire to a fully seated position in the archwire slot. Many orthodontists prefer active self-ligating systems because the lack of free space in the archwire slot in a labial-lingual direction improves rotational control of the associated tooth in directions about its long axis.

In some instances, orthodontists change the size of the archwires as treatment progresses. For example, during early stages of treatment a small diameter round archwire may be used when some teeth are located a significant distance from their ultimate desired positions. In those instances, a relatively small diameter archwire can be bent sufficiently to engage each bracket without imposing undue force on the patient's teeth. As treatment progresses and the teeth move closer to their intended destination, the orthodontist may replace the archwire with a somewhat larger and stiffer archwire having a rectangular cross-sectional shape. Rectangular archwires provide somewhat better control over movement of the tooth as it is moved closer to its ultimate destination.

Certain self-ligating brackets have archwire slots with an effective size that functions either in the active or passive mode in accordance with the overall labial-lingual dimension of the selected archwire. As an example, there may be an effective space in the archwire slot in a labial-lingual direction when a small diameter archwire is used such that the system functions in a passive mode. The same system may function in an active mode when a larger archwire is selected.

However, the self-ligating brackets described above are not entirely satisfactory, in that the choice of an active system or a passive system is somewhat limited. For example, the practitioner may determine during the course of treatment that a passive system may be desirable even when relatively large archwires have been selected. However, the practitioner in such instances may not be able to use a relatively large archwire in a passive mode if the effective archwire slot is relatively small, unless each of the brackets is replaced with a bracket having a larger effective archwire slot.

SUMMARY OF THE INVENTION

The present invention relates to a self-ligating orthodontic bracket with a dual mode latch that enables the bracket and the associated archwire to function either in an active or passive mode. In particular, the latch is movable to any one of three positions:

1) A fully opened position for insertion or removal of an archwire;
2) A first closed position wherein the latch actively engages the archwire for use in active orthodontic therapy; and
3) A second closed position wherein the latch is spaced from the archwire for passive orthodontic therapy.

The present invention combines both passive and active mode into one bracket and enables the orthodontist to choose which mode is best suited for the particular treatment at hand. The invention is useful for any type of self-ligating bracket, and can be adapted for use with essentially all types of known latches. For example, the latch may be a generally U-shaped sliding clip, a pivotal swinging cover, a sliding plate, a movable wire bail or other latch as may be desired.

In more detail, the invention in one aspect comprises an orthodontic bracket that includes a base, a body extending from the base and an archwire slot extending in the body. A latch is movable relative to the body along a generally straight path extending in a generally occlusal-gingival direction. The latch is movable to a slot open position to permit insertion or removal of an archwire from the archwire slot. The latch is movable to a first closed position wherein the latch engages the archwire for active orthodontic therapy. The latch is also movable to a second closed position wherein the latch is spaced from the same archwire for passive orthodontic therapy.

The invention in another aspect also comprises an orthodontic bracket that includes a base, a body extending from the base and an archwire slot extending in the body. In this aspect, a latch is pivotally movable relative to the body about an axis generally parallel to the direction of extension of the archwire slot. The latch is movable to a slot-open position to permit insertion or removal of an archwire from the archwire slot. The latch is movable to a first closed position wherein the latch engages the archwire for active orthodontic therapy. The latch is movable to a second closed position wherein the latch is spaced from the same archwire for passive orthodontic therapy.

A further aspect of the invention is also directed toward an orthodontic bracket that includes a base and a body extending from the base. In this aspect, a pair of mesial tiewings are connected to the body and are spaced apart from each other. A pair of distal tiewings are also connected to the body and spaced apart from each other. An archwire slot extends in the space between the pair of mesial tiewings and in the space between the pair of distal tiewings. The pair of mesial tiewings is spaced from the pair of distal tiewings to present a channel therebetween. The bracket also includes a latch and a hinge pivotally connecting the latch and the body for movement of the latch relative to the body in the channel to a slot-closed position for retaining an archwire in the archwire slot and a slot-open position to permit insertion or removal of an archwire from the archwire slot. The latch includes a pair of arms that extend away from each other in a generally mesial-distal direction. The arms extend over the archwire slot labially over the space between the pair of mesial tiewings and over the space between the pair of distal tiewings.

These and other aspects of the invention are described in more detail in the text that follows and are illustrated in the accompanying drawings.

DETAILED DESCRIPTION OF THE PREFERRED EMBODIMENTS

Figure 1:
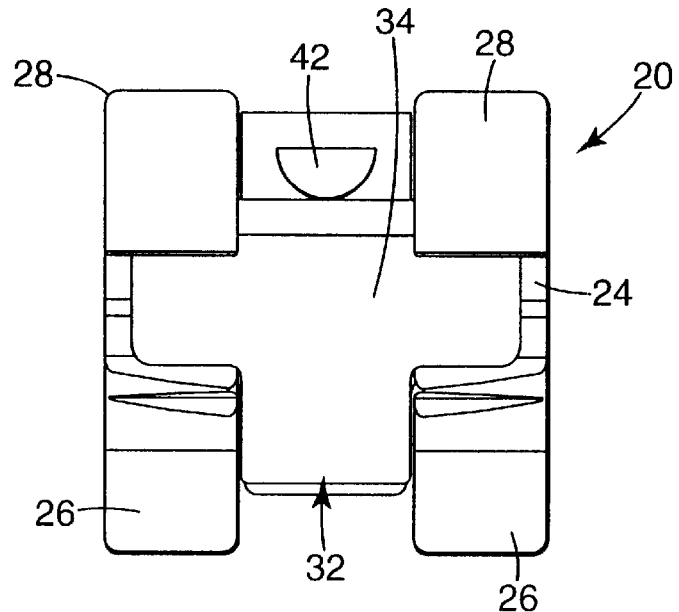
FIG. 1 is a front elevational view of a self-ligating orthodontic bracket constructed in accordance with one embodiment of the present invention, wherein a sliding latch of the bracket is shown in a second closed position.

An orthodontic bracket 20 according to one embodiment of the invention is shown in FIGS. 1–5. The bracket 20 includes a base 22 (FIG. 2 only) that is adapted for direct bonding to a surface of a tooth. The base 22 preferably has a compound contour that matches the convex shape of the tooth, and optionally is provided with grooves, undercuts, particulates, adhesion-promoting coatings or any combination thereof in order to enhance bonding. The base 22 can be integral with or initially separate from the body 24.

The bracket 20 also includes a body 24 that extends outwardly from the base 22. A pair of spaced apart occlusal tiewings 26 and a pair of spaced apart gingival tiewings 28 are integrally connected to the body 24. An archwire slot 30 extends in a mesial-distal direction in the body 24 and is located in a space between an occlusal tiewing 26 and a gingival tiewing 28 near a mesial side of the body 24 and also in a space between an occlusal tiewing 26 and a gingival tiewing 28 near a distal side of the body 24.

The bracket 20 also includes a latch 32 that is movable relative to the body 24. In this embodiment, the latch 32 comprises a generally U-shaped, resilient spring clip having a central, occlusal recurve portion as can be best appreciated by reference to FIGS. 3–5. The latch 32 includes a labial section 34 and a lingual section 36 which optionally has a length that is longer than the length of the labial section 34.

The body 24 also includes a rectangular channel 38 that extends in a generally occlusal-gingival direction and is located lingually of the archwire slot 30. The lingual section 36 of the latch 32 is received in the channel 38. Although not shown in the drawings, in embodiments of the invention where the base 22 is initially separate from the body 24, the channel 38 is optionally located on a lingual wall of the body 24 to facilitate manufacture by molding process, a milling process or the like, and the lingual side of the channel 38 is subsequently enclosed by the base 22 once the base 22 is connected to the body 24. (In FIGS. 3–5, the cross-sectional view has been taken through the tiewings 26, 28 through a labial portion of the bracket 20, but also through the central occlusal-gingival axis of the body 24 in a lingual portion of the bracket 20 in order to show the channel 38 and lingual latch section 36).

The latch 32 is movable relative to the body 24 to any one of three positions: a slot-open position, a first closed position and a second closed position. In FIG. 5, the latch 32 is illustrated in the slot-open position, where an outer end portion of the labial section 34 is located occlusally of the archwire slot 30 to enable removal or insertion of an archwire 40 (FIGS. 3–5 only) in the archwire slot 30. In the slot-open position of the latch 30, the outer end portion of the labial section 34 rests on a labial-facing surface of the occlusal tiewings 26. The lingual section 36 of the latch 32 has a labially extending protrusion 42 that engages a shoulder in the channel 38 as shown in FIG. 5 to function as a stop and limit further motion of the latch 32 in an occlusal direction. As such, the protrusion 42 substantially prevents the latch 32 from unintentionally separating from the body 24.

Figure 4:
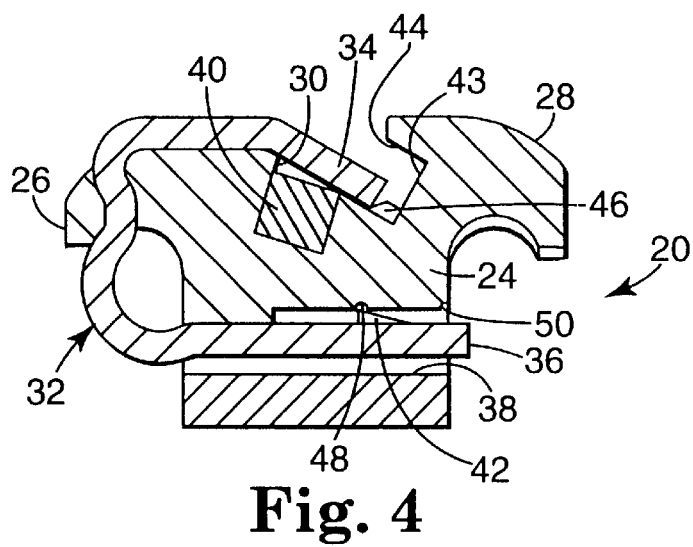
FIG. 4 is a view somewhat similar to FIG. 3 except that the latch has been moved to a first closed position.
Figure 5:
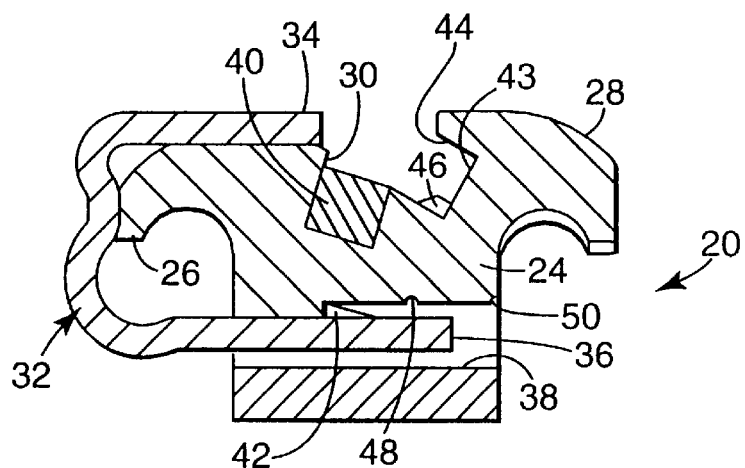
FIG. 5 is a view somewhat similar to FIGS. 3 and 4 except that the latch has been moved to a slot-open position to permit insertion or removal of an archwire.

FIG. 4 illustrates the latch 32 in its first closed position, and in this position the outer end portion of the labial section 34 of the latch 32 engages the archwire 40 for active orthodontic therapy. The resilient nature of the latch 32 enables the labial section 34 to urge the archwire 40 in a lingual direction and toward a fully seated orientation at the bottom (i.e., in contact with the lingual wall) of the archwire slot 30. When in the first closed position, the contact of the latch 32 with the archwire 40 enables the practitioner to have good rotational control over movement of the tooth upon which the bracket 20 is mounted.

The outer end portion of the labial section 34 is received in a cavity 43 of each gingival tiewing 28 adjacent the archwire slot 30 when the latch 32 is in its first closed position. Each cavity 43 has a labial wall 44 that advantageously limits outward flexural movement of the outer end portion of the labial section 34 of the latch 32. In cases of severe malocclusion where the archwire 40 must be bent to a significant extent to contact the bracket body 24, the labial walls 44 prevent undue flexing of the labial latch section 34 so that the latter does not flex outwardly to a degree sufficient to permit the archwire 40 to disengage the bracket 20.

Figure 3:
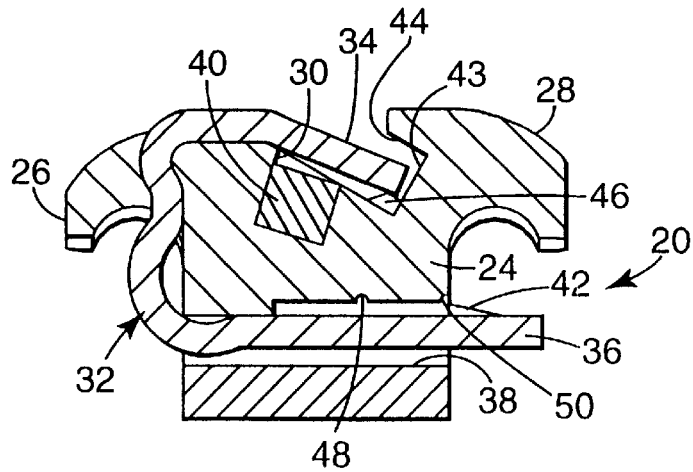
FIG. 3 is a side cross-sectional view of the bracket shown in FIG. 1.

FIG. 3 is an illustration of the latch 32 in its second closed position which in this embodiment coincides with the gingival extent of its path of travel. In the second closed position, the labial latch section 34 is received in the cavities 43, and the labial walls 44 function as described above.

The bracket body 24 includes at least one ramp portion 46 that engages the outer end portion of the labial latch section 34 when the latch 32 is moved to its second closed position. The ramp portion 46 protrudes outwardly in a labial direction, and consequently causes the flexible latch 32 to spread apart. More specifically, the outer end portion of the labial latch section 34 is cammed or deflected outwardly in a labial direction as the latch 32 is moved in a gingival direction from its first closed position to its second closed position. Preferably, the ramp portion 46 is located in the cavities 43 as well as on the labially facing surface of the body 24 in the area between the gingival tiewings 28, although other locations are also possible.

When the latch 32 is in its second closed position, the labial section 34 is somewhat spaced from the archwire 40 when the archwire 40 is fully seated in the archwire slot 30 as shown in FIG. 3 and thus provides passive orthodontic therapy. When the archwire 40 is seated in the archwire slot 30, the ramp portion 46 prevents the labial latch section 34 from engaging the underlying archwire 40 or urging the archwire 40 in a lingual direction. It is believed by some that the use of passive orthodontic therapy reduces sliding friction between the archwire and the associated brackets and as a result decreases the length of time needed for orthodontic treatment.

Preferably, the bracket 20 includes releasable locking structure that prevents unintentional movement of the latch 32 from at least one of the first closed position or the second closed position, and optionally also from the slot-open position. In the embodiment depicted in FIGS. 1–5, releasable locking structure is provided by two detents 48, 50 adjacent the labial side of the channel 38. When the latch 32 is in the first closed position, the protrusion 42 is received in the detent 48. When the latch 32 is in the second closed position, the protrusion 42 is received in the detent 50.

The detents 48, 50 are of sufficient depth in a labial direction to prevent unintentional movement of the latch 32 during the ordinary course of treatment. However, the latch 32 has sufficient flexibility to enable the lingual section 36 to self-deflect and flex outwardly in a lingual direction in order to disengage the detent 48 or 50 whenever the practitioner attempts to move the latch 32 from the first closed position or from the second closed position respectively.

If desired, the latch 32 may be removed from the body 24 during the course of treatment without detaching the bracket 20 from the underlying tooth. To remove the latch 32 from the body 24, the practitioner may insert a dental explorer or other fine-tipped dental instrument in the channel 38 and press the lingual latch section 36 in a lingual direction a distance sufficient to enable the protrusion 42 to clear the shoulder of the channel 38. The latch 32 can then be removed from the body 24 by moving the latch 32 in an occlusal direction. If desired, the bracket 20 can be used without the latch 32 in a manner similar to a conventional twin tiewing bracket, and conventional O-ring elastomeric ligatures or wire ligatures can be used in conjunction with the occlusal and gingival tiewings 26, 28 in order to ligate the archwire 40 in the archwire slot 30.

Figure 2:
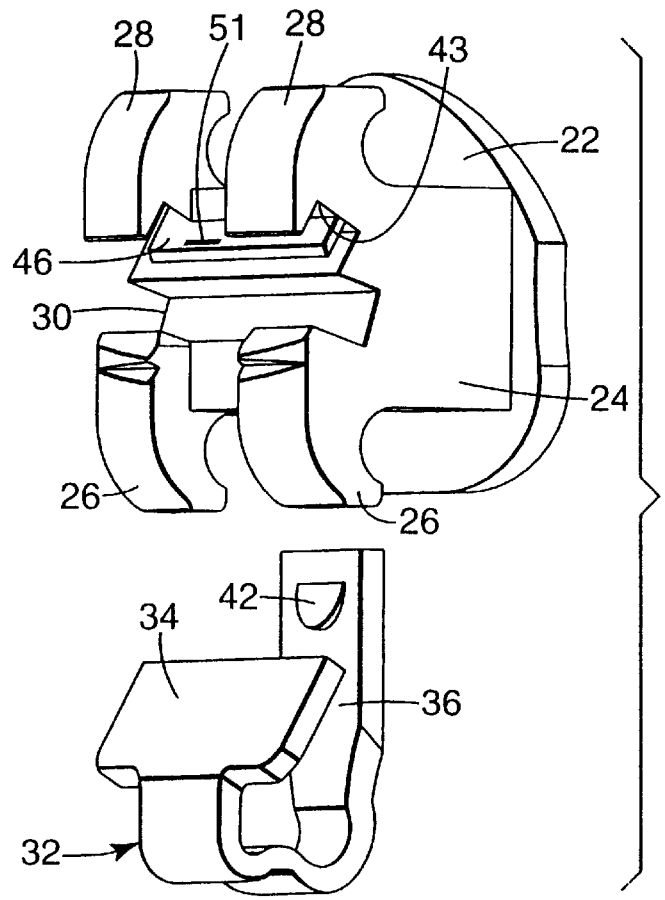
FIG. 2 is a perspective view of the bracket shown in FIG. 1, except that the latch has been removed from a bracket body for purposes of illustration.

Preferably, the outer end portion of the labial latch section 34 has arms that extend away from each other in a mesial-distal direction as can be best appreciated by reference to FIG. 2. The labial latch section 34 consequently has a "T"-shaped configuration, and the outer end portion of the labial latch section 34 extends substantially along the entire mesial-distal length of the archwire slot 30. Such enhanced length improves rotational control of the associated tooth when the bracket 20 is used in active orthodontic therapy with the latch 32 in the first closed position. When the latch 32 is moved to the slot-open position, the arms of the labial latch section 34 come to rest on a labial wall surface of the occlusal tiewings 26.

Preferably, the bracket 20 includes indicia that indicates when the latch 32 is in the first closed position and/or indicates when the latch 32 is in the second closed position. As an example, the labial-facing surface of the ramp portion 46 in the area between the gingival tiewings 28 may be provided with a scribe mark, a colored ink mark or a laser mark 51 (see FIG. 2) that serves as indicia. When the latch is in the second closed position, the outer end portion of the labial latch section 34 covers the mark 51, indicating to the practitioner that the latch 32 has reached its limit of travel in a gingival direction. As another example, the occlusal or gingival tiewings 26, 28 are provided with indicia that is aligned with other indicia affixed to the labial latch section 34 when the latch 32 is in the first closed position. The indicia allows the practitioner to readily confirm that the latch 32 is situated in its selected first or second closed position.

The bracket body 24 may be made of any suitable material, such as metal, plastic or ceramic. Suitable metallic materials include Series 300 stainless steels. The latch 32 is preferably made of a resilient metal or metallic alloy such as series 300 stainless steel. Optionally, the latch 32 may be made of a shape memory, superelastic alloy such as nitinol or beta titanium.

Figure 6:
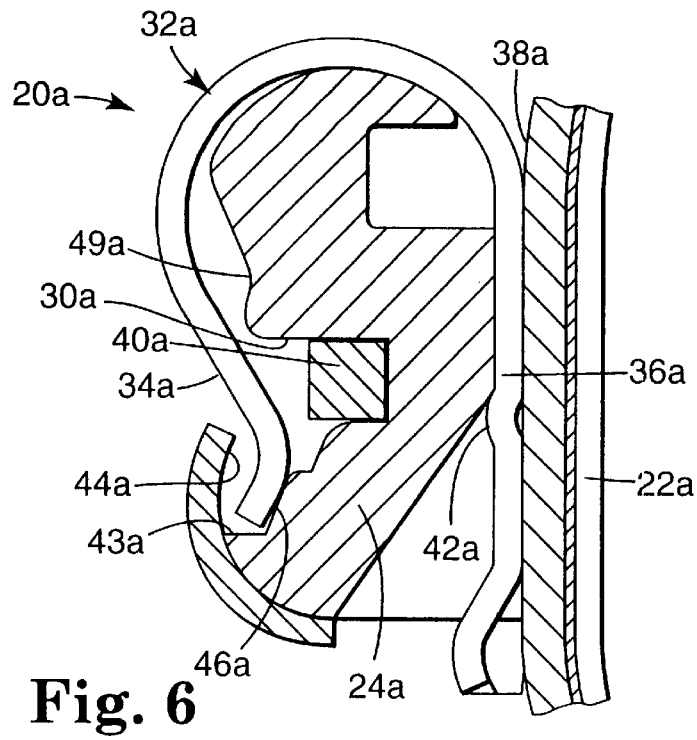
FIG. 6 is a side cross-sectional view of an orthodontic bracket constructed in accordance with another embodiment of the invention.

FIG. 6 is an illustration of another embodiment of the invention, wherein a bracket 20a includes a base 22a and a body 24a extending from the base 22a. The bracket 20a is a modification of the self-ligating bracket shown in U.S. Pat. No. 4,492,573, the disclosure of which is expressly incorporated into the present disclosure.

The bracket 20a has an archwire slot 30a and a "U"-shaped latch 32a that is movable relative to the body 24a. The latch 32a has a lingual section 36a that is received in a channel 38a. The latch 32a also has a labial section 34a with an outer end portion that is received in a cavity 43a when the latch 32a is closed.

The cavity 43a has a ramp portion 46a that engages the outer end portion of the labial latch section 34a when the latch 32a is moved to a second closed position as depicted in FIG. 6. In the second closed position, the latch 32a is spaced from an archwire 40a received in the archwire slot 30a, and thus functions in a mode providing passive orthodontic therapy. A small, compressible protrusion 42a is located in a recess when the latch 32a in the second closed position and as a result helps retain the latch 32a in that position when desired.

The latch 32a may also be moved to a first closed position wherein the outer end portion of the labial latch section 34a disengages the ramp portion 46a and self-moves inwardly in a lingual direction to reduce the effective labial-lingual depth of the archwire slot 30a. As the latch 32a disengages the ramp portion 46a, the outer end portion contacts the archwire 40a if the archwire 40a has an appropriate labial-lingual dimension relative to the archwire slot 30a such as shown in FIG. 6. When the outer end portion of the labial latch section 34a contacts the archwire 40a, the latch 32a functions in a mode providing active orthodontic therapy.

A labial wall 44a of the cavity 43a prevents excessive outward movement of the outer end portion of the labial latch section 34a. The labial wall 44a limits outward movement of the outer end portion when the latch 32a is in the first closed position and preferably also when the latch 32a is in the second closed position. The labial wall 44a functions as a stop to prevent undue outward movement of the labial section 34a in order to substantially prevent the archwire 40a from disengaging the bracket 20a.

Although not shown, the latch 32a may also be moved to a slot-open position wherein the outer end portion of the labial latch section 34a is received in a detent 49a formed in the labial face of the bracket body 24a along an occlusal side of the archwire slot 30a. The outer end portion of the labial latch section 34a consequently functions as releasable locking structure to releasably hold the latch 32a in the slot-open position, the first closed position or the second closed position. As an alternative, a detent could be provided in the channel 38a to receive the protrusion 42a when the latch 32a is moved to the slot-open position (or, as another alternative, when the latch 32a is moved to the first closed position). Other details and aspects of the brackets 20a are similar to the bracket described in the aforementioned U.S. Pat. No. 4,492,573, and consequently a detailed description of such elements and aspects need not be provided.

Figure 7:
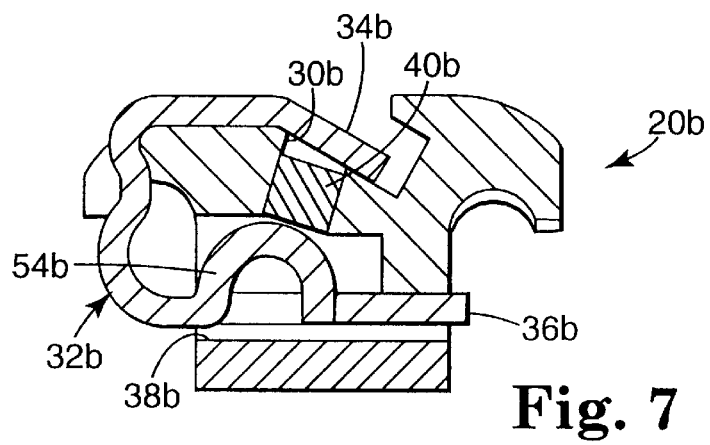
FIG. 7 is a side cross-sectional view of an orthodontic bracket that is somewhat similar to the bracket shown in FIGS. 1–5 but constructed in accordance with another embodiment of the invention.
Figure 8:
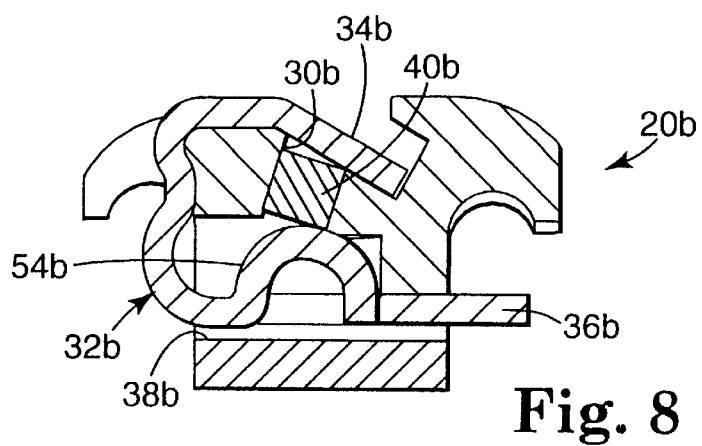
FIG. 8 is a view somewhat similar to FIG. 7 except that a latch of the bracket has been moved from a second closed position (shown in FIG. 7) to a first closed position.

An orthodontic bracket 20b according to another embodiment of the invention is illustrated is FIGS. 7 and 8. The bracket 20b is essentially the same as the bracket 20 shown in FIGS. 1–5 except for the elements and aspects set out in the paragraphs that follow.

The bracket 20b has a latch 32b that is somewhat similar to the latch 32, except that the latch 32b includes a curved tab 54b that extends in a labial direction from a lingual section 36b of the latch 32b. The tab 54b slides in a channel extension of a channel 38b of the body 24b. Optionally, the tab 54b is made by punching out and bending a middle portion of the lingual latch section 36b in an arc.

FIG. 7 is an illustration of the latch 32b as it appears when the latch 32b is in a second closed position for passive orthodontic therapy. As shown, the tab 54b is spaced in an occlusal direction from a lingual wall of the archwire 40b, and as a result the effective labial-lingual extent of the archwire slot 30b is greater than the overall lingual-labial dimension of the archwire 40b. Consequently, the space in the archwire slot 30b enables the bracket 20b to function in a mode of passive orthodontic therapy.

FIG. 8 is an illustration of the latch 32b as it appears once it is moved to a first closed position. In the first closed position, the tab 54b contacts the lingual wall of the archwire 40b and thereby urges the archwire 40b in a labial direction toward a labial section 34b of the latch 32b. When the latch 32b is in the first closed position, the effective labial-lingual extent of the archwire slot 30a is reduced and the bracket 20b functions in a mode of active orthodontic therapy. Provision of the tab 54b enables the omission of a ramp portion (such as ramp 46 in FIGS. 3–5).

Although not shown, the bracket 20b could also have a latch protrusion (somewhat similar to protrusion 42) that cooperates with channel shoulders or detents to retain the latch 32b in its selected orientation. Such a latch protrusion could be offset in a mesial or distal direction or in an occlusal direction from the position of the protrusion 42 shown in FIGS. 1–5 in order to avoid interfaring with the tab 54b. Other elements and aspects of the bracket 20b are similar to the corresponding elements and aspects of the bracket 20 described above, and consequently will not be repeated in detail.

Figure 9:
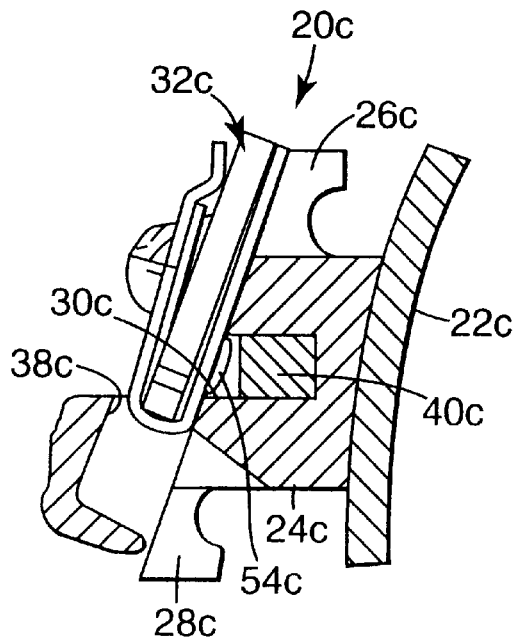
FIG. 9 is a side cross-sectional view of another self-ligating orthodontic bracket constructed in accordance with the present invention, and wherein a latch of the bracket is depicted in a first closed position.
Figure 10:
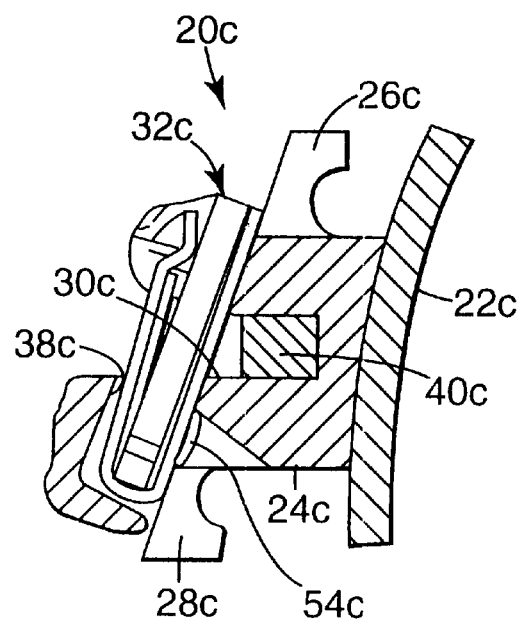
FIG. 10 is a view somewhat similar to FIG. 9 except that the latch has been moved to a second closed position.

Another embodiment of the invention is illustrated in FIGS. 9 and 10 which show a bracket 20c having a base 22c and a body 24c extending outwardly from the base 22c. Except for the elements and aspects as noted in the following paragraphs, the bracket 20c is essentially the same as the self-ligating bracket described in U.S. Pat. No. 5,613,850, the disclosure of which is expressly incorporated into the present disclosure.

The bracket 20c includes a latch 32c having a generally flat configuration. The latch 32c is slidable along a channel 38c that extends in a generally occlusal-gingival direction and is located labially of an archwire slot 30c. The channel 38c is comprised of four slots that are formed in facing sections of a pair of occlusal tiewings 26c and a pair of gingival tiewings 28c. Only one of each of the tiewings 26c, 28c is depicted in the cross-sectional view of FIGS. 9–10.

The latch 32c includes a flat core member and a flat spring member that is folded lengthwise around the core member.

Optionally, the flat spring member comprises a thin outer spring member and a thinner inner spring member as described in U.S. Pat. No. 5,613,850. The lingual side of the flat spring member includes a compressible bump or tab 54c that protrudes in a lingual direction.

FIG. 9 illustrates the position of the latch 32c relative to the body 24c when the latch 32c is in a first closed position. In the first closed position, the tab 54c is received in the archwire channel 30c and engages the labial side of the archwire 40c. Consequently, the bracket 20c provides active orthodontic therapy when the latch 32c is in the first closed position.

FIG. 10 illustrates the position of the latch 32c relative to the body 24c when the latch 32c is in a second closed position. In the second closed position, the tab 54c is not located in the archwire slot 30c, and the additional space in the archwire slot 30c provided by removal of the tab 54c enables the bracket 20c to provide passive orthodontic therapy. In the second closed position of the latch 32c, the tab 54c is located in a recess near a gingival side of the body 24c.

As the latch 32c is moved from its first closed position to its second closed position, the tab 54c is compressed and somewhat flattened as it passes over a labial section of the body 24c located between the archwire slot 30c and the recess mentioned above. However, once the tab 54c is moved to either the archwire slot 30c or the recess, the inherent resiliency of the tab 54c enables the tab 54c to resume its shape as shown in FIGS. 9 and 10 and consequently retain the latch 32c in either position. The compressible characteristic of the tab 54c, together with the space in the slot 30c or the recess, function as releasable locking structure to self-retain the latch 32c in either the first closed position or the second closed position.

Other elements and aspects of the bracket 20c are essentially the same as the bracket that is described in U.S. Pat. No. 5,613,850. As such, a detailed description of such other elements and aspects need not be provided.

In the embodiments shown in FIGS. 1–6, the second closed position of the latch is located between its first closed position and its slot-open position. However, it is also possible to rearrange the ramp portions, tabs, etc. so that the first closed position of the latch is located between its second closed position and its slot-open position if desired.

Figure 11:
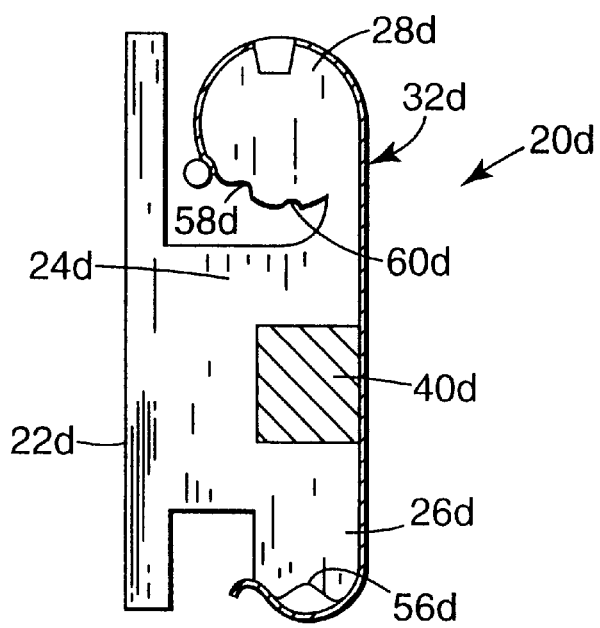
FIG. 11 is side elevational view of a self-ligating bracket constructed in accordance with yet another embodiment of the invention.

A self-ligating orthodontic bracket 20d according to another embodiment of the invention is depicted in FIG. 11. With the exception of the elements and aspects in the text that follows, the bracket 20d is essentially the same as the orthodontic bracket described in U.S. Pat. No. 4,712,999, the disclosure of which is expressly incorporated into the present disclosure.

The bracket 20d includes a base 22d and a body 24d that extends outwardly from the base 22d. A single occlusal tiewing 26d and a single gingival tiewing 28d are connected to the body 24d. An archwire slot 30d extends through the body 24d in a mesial-distal direction and is located between the occlusal tiewing 26d and the gingival tiewing 28d.

The bracket 20d also includes a latch 32d that, in this instance, comprises a hinged, swinging plate or cover. The latch 32d is pivotally movable relative to the body 24d in an arc about a reference axis parallel to the longitudinal axis of the archwire slot 30d. A gingival end portion of the latch 32d has a somewhat semi-cylindrical shape and is pivotally received on the generally cylindrical gingival tiewing 28d. An occlusal end portion of the latch 32d is also curved in the shape of a partial cylinder, and generally matches the configuration of the partially cylindrical occlusal side of the occlusal tiewing 26d. The occlusal end portion of the latch 32d serves as a catch as described below.

The occlusal tiewing 26d includes a notch 56d that extends in a mesial-distal direction. Preferably, the gingival tiewing 28d also includes notches 58d, 60d which extend in parallel, spaced apart relation in a mesial-distal direction. Preferably all of the notches 56d, 58d, 60d extend in a direction parallel to the longitudinal axis of the archwire slot 30d.

In FIG. 11, the latch 32d is shown in a first closed position wherein a lingual wall section of the latch 32d contacts the archwire 40d and urges the latter toward a fully seated position in the archwire slot 30d. The bracket 20d operates in an active orthodontic therapy mode when the latch 32d is in the first closed position. The latch 32d is resilient, and the mating shapes of the occlusal end portion of the latch 32d and the occlusal tiewing 26d provide releasable locking structure to ensure that the latch 32d remains in the first closed position when desired.

Optionally, the latch 32d can be moved to a second closed position (not shown). In the second closed position of the latch 32d, the curved tip of the occlusal end portion of the latch 32d is caught in the notch 56d, and the end of the gingival end portion of the latch 32d is received in the notch 58d. In the second closed position of the latch 32d, the labial wall sections of the latch 32d are spaced from the archwire 40d and enable the bracket 20d to operate in a mode providing passive orthodontic therapy. The notches 56d, 58d provide releasably locking structure to help ensure that the latch 32d remains in the second closed position when desired.

Although not shown, the latch 32d can also be swung outwardly and opened to a slot-open position to enable removal or insertion of the archwire 40d. In the slot-open position, the outer end of the gingival end portion of the latch 32d rests in the notch 60d in order to help retain the latch 32d in the slot-open position as long as desired. Other elements and aspects of the bracket 20d are similar to the elements and aspects of the self-ligating bracket described in the aforementioned U.S. Pat. No. 4,712,999.

Figure 12:
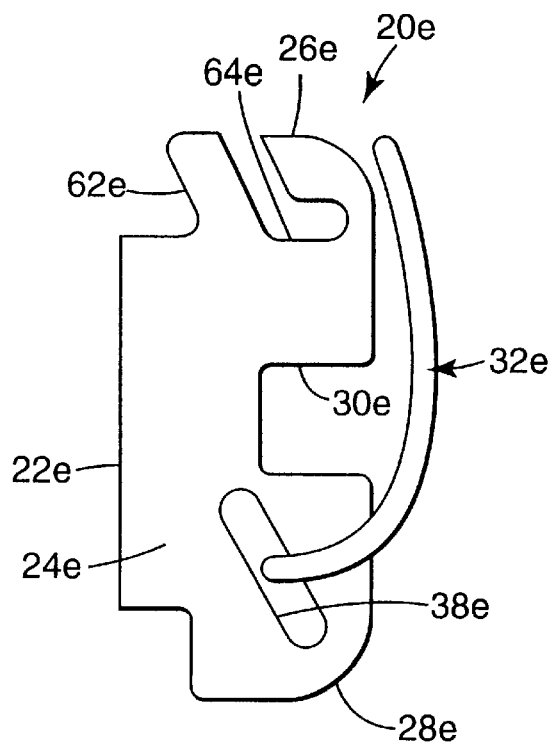
FIG. 12 is a side elevational view of a self-ligating orthodontic bracket constructed in accordance with still another embodiment of the invention.

An orthodontic bracket 20c according to yet another embodiment of the invention is illustrated in FIG. 12. Except for the elements and aspects as noted below, the bracket 20e is essentially identical to the self-ligating bracket described in U.S. Pat. No. 4,149,314, the disclosure of which is expressly incorporated into the present disclosure.

The bracket 20e includes a base 22e and a body 24e that extends outwardly from the base 22e. A pair of occlusal tiewings 26e (only one is shown) and a pair of gingival tiewings 28e (only one is shown) are connected to the body 24e. An archwire slot 30e extends in a mesial-distal direction in the body 24e between the occlusal tiewings 26e and the gingival tiewings 28e.

The bracket 20e includes a latch 32e that, in this embodiment, is made of a section of round wire and functions somewhat similar to a swinging bail. The latch 32e has a generally "C"-shaped configuration, with end sections that are bent inwardly toward each other and extend into a channel 38e of the bracket body 24e adjacent the gingival tiewing 28c.

The occlusal tiewings 26e have a notch or undercut 62e as well as a somewhat L-shaped notch 64e, both of which extend in a generally mesial-distal direction through the occlusal tiewings 26e. The occlusal end portion of the latch 32e is releasably received in either the notch 64e or the area of the tiewing undercut 62e as desired.

When the occlusal portion of the latch 32e is received in the tiewing undercut 62e, the middle portion of the latch 32e bears against an archwire (not shown) to urge the archwire in a lingual direction toward a fully-seated position against the lingual wall of the archwire slot 30e. When the occlusal portion of the latch 32c is received in the tiewing undercut 62e, the latch 32e is in a first closed position and the space between the latch 32e and the archwire enables the bracket 20e to provide active orthodontic therapy (assuming the archwire is of appropriate size).

When the occlusal portion of the latch 32e is received in the notch 64e, the effective labial-lingual dimension of the archwire slot 30e increased and is somewhat greater than the overall labial-lingual extent of the archwire such that free space is provided along either the labial side of the archwire or the lingual side of the archwire or both. When the occlusal portion of the latch 32e is received in the notch 64e, the latch 32e is in a second closed position and the bracket 20e provides passive orthodontic therapy.

The latch 32e is preferably made of a section of wire stock having a round cross-sectional configuration, although the use of wire stock having other configurations is also possible. The wire may be relatively stiff, or alternatively may be somewhat resilient. Optionally, the wire is stretched to insert the occlusal portion of the latch 32e in the tiewing undercut 62e or the notch 64e. The latch 32e, the undercut 62e and the notch 64e all have appropriate sizes and shapes (that may deviate from that shown in the drawings) to help ensure that the latch 32e remains in the undercut 62e or notch 64e, as selected, during the desired course of treatment.

Other elements and aspects of the bracket 20e are similar to the self-ligating bracket in described in U.S. Pat. No. 4,149,314. The reader is referred to that patent for additional description if desired.

Figure 14:
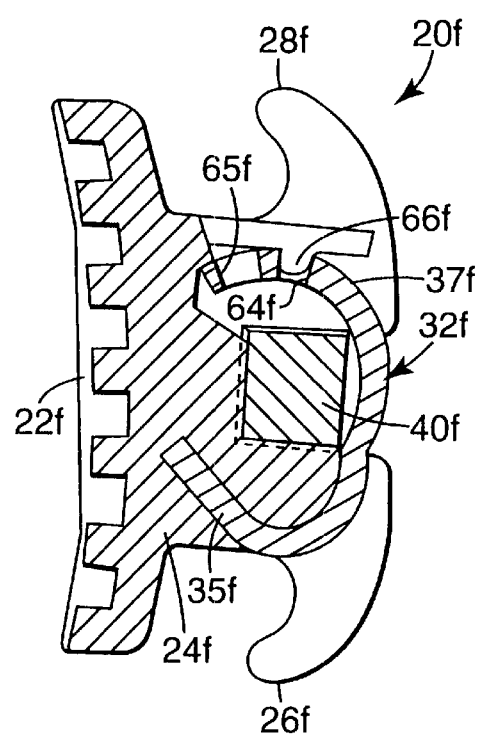
FIG. 14 is a side cross-sectional view of the bracket depicted in FIG. 13, except that the latch is shown in a first closed position for use in active orthodontic therapy.
Figure 13:
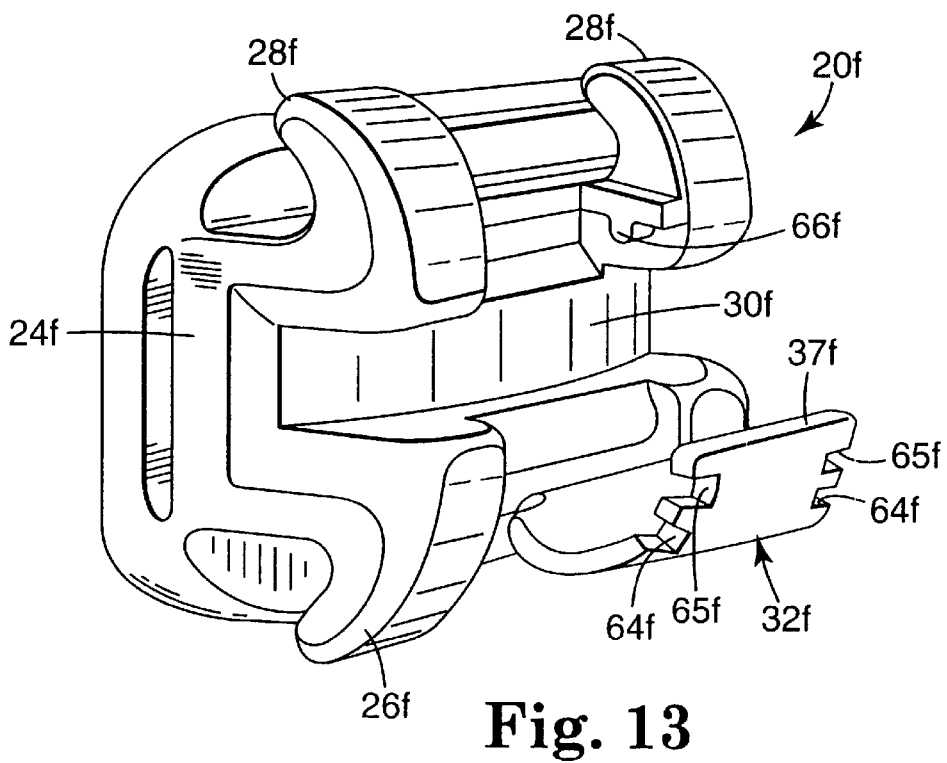
FIG. 13 is a perspective view of a self-ligating bracket constructed in accordance with another embodiment of the invention, and wherein a latch of the bracket is depicted in a slot-open position.

An orthodontic bracket 20f that is constructed in accordance with yet another embodiment of the invention is illustrated in FIGS. 13 and 14. Except for the elements and aspects described in the following paragraphs, the bracket 20f is essentially the same as the self-ligating bracket described in U.S. Pat. No. 5,711,666, the disclosure of which is expressly incorporated by reference into the present disclosure.

The bracket 20f has a base 22f and a body 24f that extends outwardly from the base 22f. The bracket 20f also includes a pair of occlusal tiewings 26f and a pair of gingival tiewings 28f that are each connected to the body 24f. An archwire slot 30f extends through the body 24f in a generally mesial-distal direction and is adapted to receive an orthodontic archwire 40f that is shown only in FIG. 14.

A latch 32f of the bracket 20f is made of a resilient material, and has an occlusal section 35f that is captured and fixed to an occlusal portion of the bracket body 24f. A gingival section 37f of the latch 32f has two opposed pairs of side notches 64f, 65f. The latch 32f has sufficient resilience to enable it to be bent from a slot-open position as illustrated in FIG. 13 into either a first closed position or a second closed position.

The bracket 20f also includes a pair of catches 66f that are connected to the occlusal tiewings 26f. In FIGS. 13 and 14, only one of the catches 66f is shown.

FIG. 14 is an illustration of the latch 32f in a first closed position wherein the catches 66f are received in the notches 64f. In the first closed position, the latch 32f contacts the archwire 40f and urges the latter toward a position of full seating contact with the lingual side of the archwire slot 30f. The latch 32f enables the bracket 20f to provide active orthodontic therapy when the latch 32f is in the first closed position.

Although not shown in the drawings, the latch 32f can also be moved to a second closed position wherein a lingual wall section of the latch 32f is spaced from a lingual wall of the archwire slot 40f a distance sufficient to provide passive orthodontic therapy. In the second closed position of the latch 32f, the catches 66f are received in respective notches 65f. The effective labial-lingual depth of the archwire slot 30f is greater when the latch 32f is in the second closed position than when the latch 32f is in the first closed position.

Other elements and aspects of the bracket 20f are essentially the same as the elements and aspects of the self-ligating orthodontic bracket described in U.S. Pat. No. 5,711,666. Optionally, the bracket 20f may be provided with two pair of catches and one pair of notches if desired, and/or the position of the notches and catches may be swapped.

Figure 15:
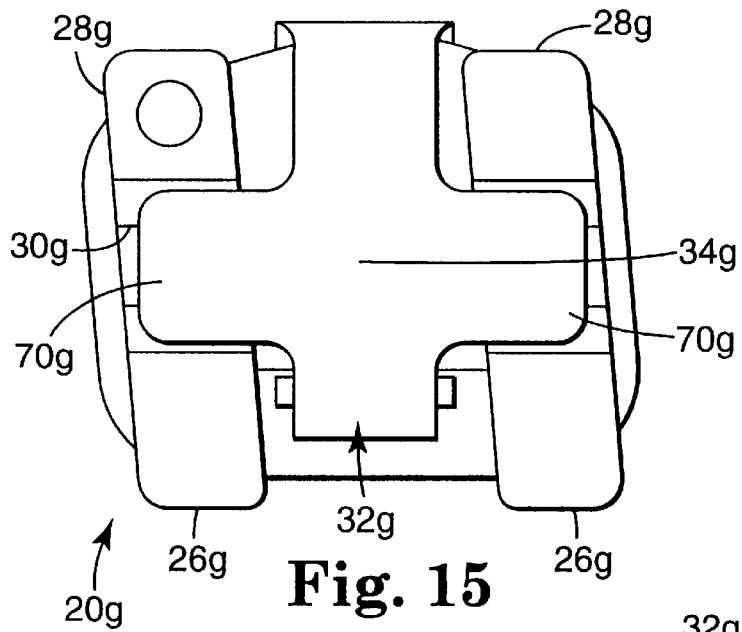
FIG. 15 is a front elevational view of a self-ligating bracket constructed in accordance with a further embodiment of the invention.
Figure 16:
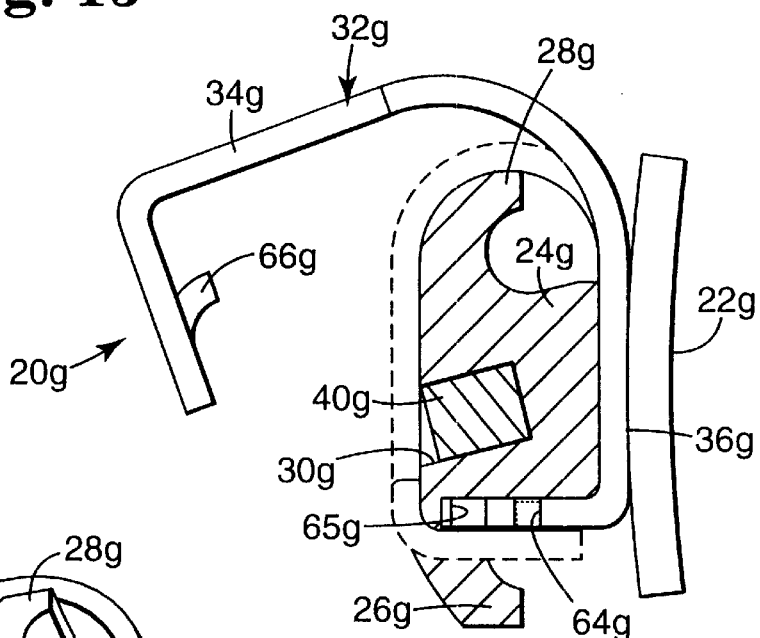
FIG. 16 is a side cross-sectional view of the bracket illustrated in FIG. 15, wherein a latch of the bracket is shown in full lines as it appears when used in active orthodontic therapy and is shown in dashed lines as it appears when moved to a slot-open position.
Figure 17:
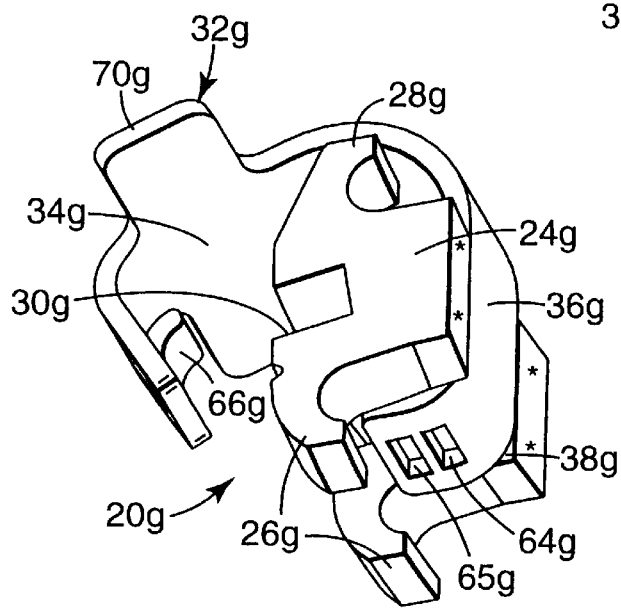
FIG. 17 is a perspective view of the bracket shown in FIGS. 15 and 16 wherein the latch has been moved to the slot-open position and a base of the bracket has been omitted to depict a lingual channel of the bracket body.
Figure 18:
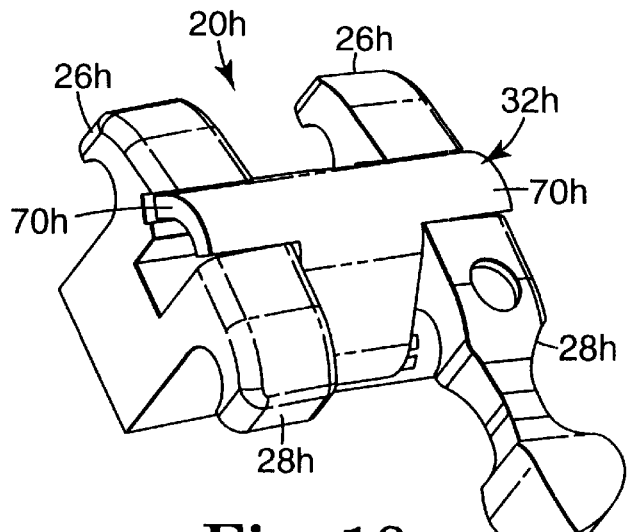
FIG. 18 is a perspective view of a self-ligating bracket constructed in accordance with still another embodiment of the invention, and wherein a latch of the bracket is depicted in a first closed position.
Figure 19:
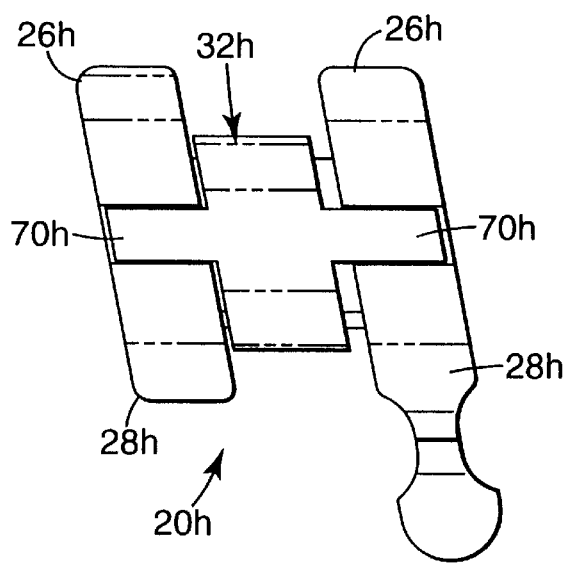
FIG. 19 is a front elevational view of the bracket shown in FIG. 18.

An orthodontic bracket 20g constructed in accordance with still another embodiment of the invention is illustrated in FIGS. 15–17. The bracket 20g includes a base 22g that is shown in FIGS. 15 and 16 but is omitted in FIG. 17. A body 24g extends outwardly from the base 22g in a labial direction.

A pair of occlusal tiewings 26g and a pair of gingival tiewings 28g are integrally connected to the body 24g. An archwire slot 30g extends through the body 24g in a generally mesial-distal direction. The archwire slot 30g is adapted to receive an orthodontic archwire 40g that is depicted only in FIG. 16.

A latch 32g is made of a resilient material such as stainless steel, and optionally is made of an alloy having shape memory and/or superelastic characteristics such as nitinol or beta-titanium. The latch 32g when closed has a ring-shaped configuration and encircles a central portion of the body 24g along its lingual, labial, occlusal and gingival sides. A lingual section 36g of the latch 32g is received in a lingual channel 38g of the body 24g as illustrated in FIGS. 16 and 17. The latch 32g is preferably not fixed to the bracket body 24g but is retained the channel 54g by the base 22g. Once the latch 32g is in place as shown in the drawings, the base 22g is fixed to the body 24g by spot welds, by an electron-beam process or the like at the locations marked "*" in FIG. 17.

The latch 32g includes two notches 64g, 65g on one end section and an inwardly protruding ear or catch 66g on an opposite end section. In the embodiment shown in the drawings, the notches 64g, 65g are located on the end section of the latch 32g that is located directly adjacent an occlusal side of the bracket body 24g, while the other end section of the latch 32g that includes the catch 66g is provided on the opposite end section. Alternatively, however, the catch 66g could be provided on the end section of the latch 32g adjacent the occlusal side of the bracket body 24g, while the notches 64g, 65g could be located on the remaining end section of the latch 32g.

The catch 66g is adapted to be received in either of the notches 64g, 65g when the latch 32g is moved toward a closed position. In FIG. 16, the latch 32g is depicted in dashed lines in a first closed position wherein the catch 66g is received in the notch 64g. In the first closed position (also shown in FIG. 15), a labial section 34g of the latch 32g contacts the archwire 40g when the latter is fully seated in the archwire slot 30g such that the bracket 20g provides active orthodontic therapy.

When the catch 66g is received in the notch 65g, the latch 32g is in a second closed position wherein the labial section 34g is spaced from the same archwire 40g when the latter is fully seated in the archwire slot 30g. Consequently, the effective depth of the archwire slot 30g is greater in a labial-lingual direction when the latch 32g is in the second closed position as compared to when the latch 32g is in the first closed position. In the second closed position, the labial section 34g provides sufficient space within the archwire slot 30g in a labial-lingual direction to enable the bracket 20g to provide passive orthodontic therapy.

Preferably, the latch 32g includes two arms 70g that extend outwardly away from each other in a mesial-distal direction. The arms 70g extend over the archwire slot 30g in the space between the occlusal and gingival tiewings 26g, 28g located near the mesial side of the bracket as well as in the space between the occlusal and gingival tiewings 26g, 28g located near the distal side of the bracket 20g. The arms 70g preferably contact the archwire 40g when the latch 32g is in the first closed position in order to enhance rotational control over the tooth upon which the bracket 20g is mounted.

A hand instrument such as a dental scaler or probe may be used to release the catch 66g from either of the notches 64g, 65g when desired. Preferably, as the latch 32g is moved to a slot open position as shown in FIG. 17 and also shown by the full lines in FIG. 16, the majority of bending movement of the latch 32g occurs in the area adjacent the gingival side of the bracket body 24g and the gingival side of the gingival tiewings 28g, so that the outer end section of the latch 32g that normally extends over the labial and occlusal side of the bracket body 24g when the latch 32g is closed retains its generally "L"-shaped configuration. Since the latch 32g is preferably not fixed to the body 24g, the latch 32g can shift slightly along the channel 38g as may be necessary to facilitate placement of the catch 66g in the selected notch 64g, 65g, and particularly in the notch 64g. Optionally, in some embodiments the latch 32g may be provided with only one notch (such as notch 64g) if desired so that only passive or active therapy is provided with a given archwire.

Another embodiment of the invention is shown in FIGS. 18–22, and concerns a bracket 20h that has a base 22h and a body 24h that extends outwardly from the base 22h. In the illustrated embodiment, the base 22h is integral with the body 24h. As another option, however, the base 22h may be initially separate from the body 24h and subsequently fixed together, and the base 22h may extend outwardly past the body 24h in occlusal-gingival directions and/or mesial-distal directions.

The bracket 20h also includes a pair of occlusal tiewings 26h and a pair of gingival tiewings 28h, all of which are integrally connected to the body 24h. One of the gingival tiewings 28h is integrally connected to a hook as shown in the drawings, although the hook is optional. An archwire slot 30h extends in a generally mesial-distal direction across a labial side of the bracket 24h, including in the space between the occlusal and gingival tiewings 26h, 28h near a mesial side of the bracket 20h and in the space between the occlusal and gingival tiewings 26h, 28h near a distal side of the bracket 20h.

Figure 20:
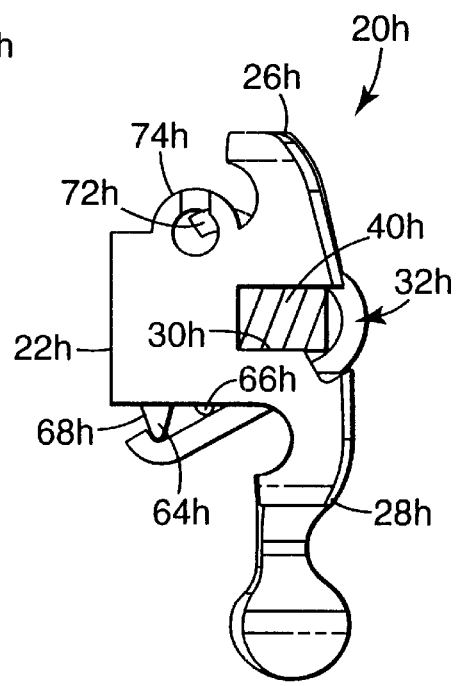
FIG. 20 is a side elevational view of the bracket shown in FIGS. 18 and 19.
Figure 21:
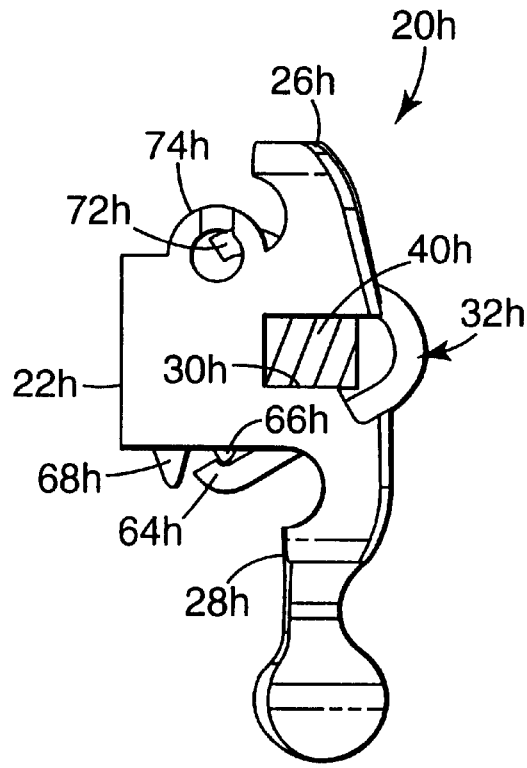
FIG. 21 is a view somewhat similar to FIG. 20 except that the latch has been moved to a second closed position for use of the bracket in passive orthodontic therapy.
Figure 22:
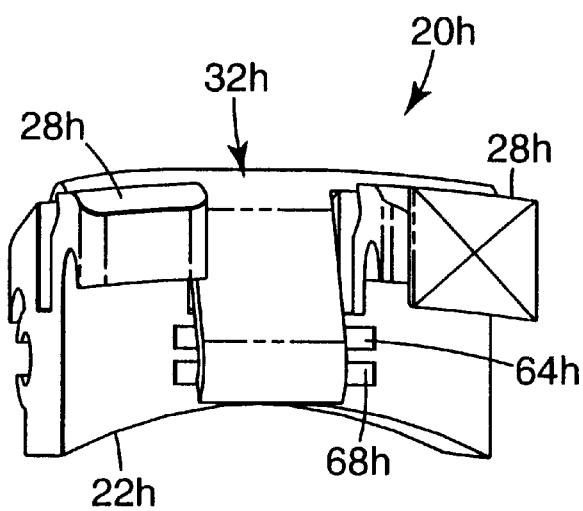
FIG. 22 is a view looking toward an occlusal side of the bracket shown in FIGS. 18–20.

The bracket 20h also includes a latch 32h that is movable relative to the body 24h. Preferably, the latch 32h is pivotally movable relative to the body 24h about a reference axis that extends generally parallel, and more preferably extends parallel, to the longitudinal axis of the archwire slot 30h. The latch 32h is swingable to any one of three positions: a first closed position as shown in FIG. 20, a second closed position as shown in FIG. 21 and a slot-open position. The slot-open position is not illustrated in the drawings, but in this position the latch 32h is opened sufficiently to enable an archwire (such as an archwire 40h as shown in FIGS. 20 and 21) to be inserted into or removed from the archwire slot 30h.

The latch 32h has an occlusal end section or crossbar 72h that extends in a mesial-distal direction. The crossbar 72h is received in passages of two cylindrical hinge sections 74h that are integrally connected to the body 24h. Each of the hinge sections 74h is located lingually beneath a respective occlusal tiewing 26h.

During manufacture of the bracket 20h, the crossbar 72h is inserted in a gingival direction through an opening and into the passages of the hinge sections 74h. Subsequently, the hinge sections 74h are crimped sufficiently so that the opening into the passageways is closed or at least partially closed. As a result, the crossbar 72h is captured in the hinge sections 74h. The crossbar 72h and the hinge sections 74h function together as a hinge to enable the latch 32h to pivotally move between the first closed position, the second closed position and the slot-open position as desired.

A pair of protruding catches 66h, 68h are integrally connected to a gingival side of the bracket body 24h. Preferably, and as shown in the drawings, each of the catches 66h, 68h has a cross-sectional shape similar to a curved, truncated prism, although shapes are also possible. Preferably, each of the catches 66h, 68h extends in a direction that is parallel to the longitudinal axis of the archwire slot 30h and the longitudinal axis of the crossbar 72h.

The latch 32h includes a gingival end section that is curved to form a notch 64h. When the latch 32h is in the first closed position as depicted in FIG. 20, the notch 64h engages the catch 68h and retains a labial section 34h of the latch 32h in contact with the archwire 40h. In the first closed position of the latch 32h, the labial section 34h contacts the labial side of the archwire 40h while the lingual side of the archwire 40h is in close, mating contact with bottom or lingual side of the archwire slot 30h, such that the bracket 20h provides active orthodontic therapy.

Preferably, and as shown in the embodiment shown in FIGS. 18–22, the latch 32h includes a pair of arms 70h connected to the labial section 34h. The arms 70h extend outwardly away from each other in opposite, mesial-distal directions, and extend across the labial side of the archwire slot 30h when the latch 32h is in either of its closed positions. The arms 70h enable the latch 32h to extend over the entire mesial-distal length of the bracket 20h and consequently provide better rotational control over movement of the tooth upon which the bracket 20h is mounted.

Preferably, the gingival tiewings 28h each include a labial groove 71h that received a gingival, outer terminal edge section of a respective arm 70h when the latch 32h is in its first closed position. The grooves 71h help retain the latch 32h in its first closed position. The latch 32h is sufficiently stiff to remain in the first closed position when desired, but is also sufficiently flexible to enable the arms 70h to disengage the grooves 71h whenever an attempt is made to move the latch 32h from its first closed position.

The curved labial section of the latch 32h is also an advantage, in that only the corners of the archwire 40h typically contact the inner, lingual side of the labial latch section. The reduced area of contact between the latch 32h and the archwire 40h reduces sliding friction. The corner of conventional archwires are typically rounded and do not cut into the labial latch section in use.

When the latch 32h is in the second closed position as shown in FIG. 21, the notch 64h is received on the catch 66h. Since the catch 66h is located labially of the catch 68h, the labial section 34h of the latch 32h is spaced a distance farther from the bottom of the archwire slot 30h when the latch 32h is in the second closed position as compared to when the latch 32h is in the first closed position. In the second closed position, the labial section 34h is spaced sufficiently from the bottom of the archwire slot 30h to provide a space along either or both of the labial and lingual sides of the archwire 40h, such that the bracket 20h functions in a passive mode.

Preferably, the latch 32h is made of a resilient metallic material such as stainless steel or the like. Optionally, the latch 32h may be made of a shape memory alloy that exhibits superelastic characteristics such as nitinol or beta-titanium. The latch 32h is sufficiently resilient to retain its generally "U"-shaped configuration and normally remain in either the second closed position or the first closed position as selected by the practitioner. However, when desired, the practitioner can use a probe, explorer or other dental instrument to bend the gingival end section of the latch 32h outwardly so that the notch 64h disengages the catch 66h or 68h, in order to open the latch 32h when desired.

The bracket 20h is a significant advantage, in that the latch 32h can be used in brackets that are angulated as shown in the drawings. In angulated brackets, the central longitudinal axis of the tiewings (such as tiewings 26h, 28h) extend at an angle other than 90 degrees relative to the longitudinal axis of the archwire slot (such as archwire slot 30h). However, the latch 32h is also useful in conjunction with non-angulated brackets wherein in the longitudinal axis of the tiewings extends in a direction perpendicular to the longitudinal axis of the archwire slot. As an option according to alternative embodiments, one of the catches 66h, 68h may be eliminated to provide only one mode of treatment if desired. As another option, the bracket 20h may be provided with 2 notches and only one catch in order to provide both active and passive treatment modes.

The present invention in its various embodiments may also be used in a treatment program that provides active therapy when either of two differently-sized archwires are employed. For example, the latch in the first closed position may provide active therapy when used with a rectangular archwire having a certain overall labial-lingual dimension, and in the second position may be used to provide active therapy with a rectangular archwire having a somewhat larger overall labial-lingual dimension. As a result, moving the latch from the first closed position to the second closed position can enable the use of larger archwires (at least in a labial-lingual dimension) without significantly increasing, if at all the amount of sliding friction between, the latch and the archwire. Such construction is particularly advantageous for the dental practitioner who prefers active therapy during a patient's entire course of orthodontic treatment.

A variety of modifications and additions may be made to the embodiments described in detail above without departing from the spirit of the invention. As a consequence, the invention should not be deemed limited to the specific embodiments set out above, but only by a fair scope of the claims that follow along with their equivalents.

What is claimed is:

1. An orthodontic bracket comprising:
    a base;
    a body extending from the base;
    an archwire slot extending in the body; and
    a latch movable relative to the body along a generally straight path extending in a generally occlusal-gingival direction, the latch being movable to a slot-open position to permit insertion or removal of an archwire from the archwire slot, the latch being movable to a first closed position wherein the latch engages the archwire for active orthodontic therapy, the latch also being movable to a second closed position wherein the latch is spaced from the same archwire for passive orthodontic therapy.

2. An orthodontic bracket according to claim 1, wherein the latch includes a section extending along the labial side of the archwire slot, and wherein the section is nearer to the base when the latch is in the first closed position than when the latch is in the second closed position.

3. An orthodontic bracket according to claim 1, wherein the latch has a section extending across a lingual side of the archwire slot, and wherein the section is nearer to the labial side of the bracket when the latch is in the first closed position than when the latch is in the second closed position.

4. An orthodontic bracket according to claim 3, wherein the section extends in a channel of the body adjacent a lingual side of the archwire slot.

5. An orthodontic bracket according to claim 1, wherein the latch has a generally U-shaped configuration.

6. An orthodontic bracket according to claim 1, wherein the latch has a generally flat configuration.

7. An orthodontic bracket according to claim 1, wherein the latch has a tab for contact with the archwire when the latch is in the first closed position.

8. An orthodontic bracket according to claim 7, wherein the tab extends through a channel of the body along a lingual side of the archwire slot.

9. An orthodontic bracket according to claim 1, wherein the bracket includes at least one ramp portion for moving at least a section of the clip in a labial direction when the latch is moved to the second closed position.

10. An orthodontic bracket according to claim 1, wherein the bracket includes indicia that indicates when the latch is in the first closed position or the second closed position.

11. An orthodontic bracket according to claim 10, wherein the latch includes an outer end portion, and wherein the indicia is aligned with the outer end portion of the latch when the latch is in one of the first closed position or the second closed position.

12. An orthodontic bracket according to claim 10, wherein the latch includes an outer end portion, and wherein the indicia is covered by the outer end portion when the latch is in one of the first closed position or second closed position.

13. An orthodontic bracket comprising:
    a base;
    a body extending from the base;
    an archwire slot extending in the body; and
    a latch pivotally movable relative to the body about an axis generally parallel to the direction of extension of the archwire slot, the latch being movable to a slot-open position to permit insertion or removal of an archwire from the archwire slot, the latch being movable to a first closed position wherein the latch engages the archwire for active orthodontic therapy, the latch also being movable to a second closed position wherein the latch is spaced from the same archwire for passive orthodontic therapy.

14. An orthodontic bracket according to claim 13, wherein the latch has a labial section that is nearer to the base when the latch is in the first closed position than when the latch is in the second closed position.

15. An orthodontic bracket according to claim 14, wherein the latch is hinged to the body.

16. An orthodontic bracket according to claim 14, wherein the latch is resilient and bends as it is moved from the open position to either the first closed position or the second closed position.

17. An orthodontic bracket according to claim 13, wherein the bracket includes at least one notch and at least one catch for releasably retaining the latch in at least one of the second closed position or the first closed position.

18. An orthodontic bracket according to claim 13, wherein the latch is comprised of a section of wire, and wherein the body has at least two notches to receive the wire in either the first closed position or the second closed position.

19. An orthodontic bracket comprising:

a base;

a body extending from the base;

a pair of mesial tiewings connected to the body and spaced apart from each other;

a pair of distal tiewings connected to the body and spaced apart from each other;

an archwire slot extending in the space between the pair of mesial tiewings and in the space between the pair of distal tiewings, and wherein the pair of mesial tiewings is spaced from the pair of distal tiewings to present a channel there between;

a latch; and a hinge pivotally connecting the latch and the body for movement of the latch relative to the body in the channel to a slot-closed position for retaining an archwire in the archwire slot and a slot-open position to permit insertion or removal of an archwire from the archwire slot, wherein the latch includes a pair of arms extending away from each other in a generally mesial-distal direction and extending over the archwire slot labially over the space between the pair of mesial tiewings and over the space between the pair of distal tiewings;

wherein one of the latch and the body include a notch and the other of the latch and the body include a pair of catches, wherein one of the catches is spaced labially of the other catch, wherein the latch includes a labial section, wherein the archwire slot includes a lingual side, and wherein the labial section is closer to the lingual side when the notch is received by one of the catches as compared to when the notch is received by the other of the catches.

20. An orthodontic bracket according to claim 19 wherein one of the latch and the body includes a notch, and wherein the other of the latch and the body includes a catch that is releasably received in the notch when the latch is in the slot-closed position.

21. An orthodontic bracket according to claim 19 wherein the catches are elongated and extend in a direction generally parallel to the direction of extension of the archwire slot.

22. An orthodontic bracket according to claim 19 wherein the latch includes a pair of arms that extend in a generally mesial-distal direction substantially the entire length of the archwire slot.

23. An orthodontic bracket according to claim 19 wherein the mesial tiewings and the distal tiewings have a central longitudinal axis that extends at a non-perpendicular angle relative to the direction of extension of the archwire slot.

24. An orthodontic bracket according to claim 19 wherein the latch includes a crossbar received in a passage connected to the body.

25. An orthodontic bracket according to claim 24 wherein the passage is defined by crimpable sections.

26. An orthodontic bracket according to claim 25 wherein the crimpable sections are located lingually of at least one of the tiewings.

27. An orthodontic bracket comprising:

a base;

a body extending from the base;

a pair of mesial tiewings connected to the body and spaced apart from each other;

a pair of distal tiewings connected to the body and spaced apart from each other;

an archwire slot extending in the space between the pair of mesial tiewings and in the space between the pair of distal tiewings, and wherein the pair of mesial tiewings is spaced from the pair of distal tiewings to present a channel therebetween;

a latch; and a hinge pivotally connecting the latch and the body for movement of the latch relative to the body in the channel to a slot-closed position for retaining an archwire in the archwire slot and a slot-open position to permit insertion or removal of an archwire from the archwire slot, wherein the latch includes a pair of arms extending away from each other in a generally mesial-distal direction and extending over the archwire slot labially over the space between the pair of mesial tiewings and over the space between the pair of distal tiewings;

wherein one of the latch and the body include a catch and the other of the latch and the body include a pair of notches, wherein the notches are spaced from each other, wherein the latch includes a labial section and wherein the archwire slot includes a lingual side, and wherein the labial section is closer to the lingual side when the catch is received in one of the notches as compared to when the catch is received in the other of the notches.

* * * * *

UNITED STATES PATENT AND TRADEMARK OFFICE
CERTIFICATE OF CORRECTION

PATENT NO. : 6,071,119
DATED : June 6, 2000
INVENTOR(S) : James D. Christoff, John S. Kelly and Evangelos G. Georgakis It is certified that error appears in the above-identified patent and that said Letters Patent is hereby corrected as shown below:

Column 12,
Line 42, "20c" should read --- 20e ---.
Line 61, "28c" should read --- 28e ---.

Column 13,
Line 6, "32c" should read --- 32e ---.

Signed and Sealed this

Twenty-fifth Day of September, 2001

Attest:

*Attesting Officer*

NICHOLAS P. GODICI
*Acting Director of the United States Patent and Trademark Office*